US00PP20591P2

(12) United States Plant Patent
Utecht

(10) Patent No.: US PP20,591 P2
(45) Date of Patent: Dec. 22, 2009

(54) ***PELARGONIUM* PLANT NAMED 'FISLADA'**

(50) Latin Name: *Pelargonium peltatum (L.) L'Hérit. ex Ait*
Varietal Denomination: Fislada

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/228,684

(22) Filed: Aug. 15, 2008

(51) Int. Cl.
*A01H 5/00* (2006.01)

(52) U.S. Cl. ..... Plt./332

(58) Field of Classification Search ..... Plt./332
See application file for complete search history.

(56) References Cited

OTHER PUBLICATIONS

Upov Plant Variety database 2009/02 p. 1a.*
Upov Plant Variety database 2009/02 p. 1b.*

* cited by examiner

*Primary Examiner*—Annette H Para
(74) *Attorney, Agent, or Firm*—S. Matthew Edwards

(57) ABSTRACT

A new *Pelargonium* plant named 'Fislada,' particularly distinguished by the large, brilliant purple-pink, double-type flowers, medium sized inflorescences, medium green foliage with good heat tolerance, lobed leaves with distinct zonation, small to medium sized, tight, semi-trailing plant habit, and early and continuously flowering.

1 Drawing Sheet

Latin name of the genus and species of the plant claimed: *Pelargonium peltatum* (*L.*) *L'Hérit. ex Ait.*

Varietal denomination: 'Fislada'.

BACKGROUND OF THE NEW PLANT

The present invention comprises a new *Pelargonium* (common name: ivy *Geranium*) plant, botanically known as *Pelargonium peltatum* and hereinafter referred to by the variety name 'Fislada.'

'Fislada' is a product of a planned breeding program. The new cultivar has large purple-pink, double-type flowers, medium-green, distinctly zoned foliage, and compact, small to medium sized plant habit.

'Fislada' originated from a hybridization made in the late summer of 2003 in a controlled breeding program in Hillscheid, Germany. The female parent was the commercial variety 'Colorcade Coral Pink,' U.S. Plant Pat. No. 13,563, 'Balcolcork,' with salmon-pink to light carmine-red, double flowers, zoned foliage, and about medium sized mounding and trailing plant habit.

The male parent of 'Fislada' was the commercial variety 'Fislina,' U.S. Plant Pat. No. 16,681, with salmon-pink, double flowers, medium green foliage, distinct leaf zone, and medium to tall, trailing plant habit. 'Fislada' has short to medium length of peduncles, while flower stalks of 'Fislina' are only initially short, but relatively long under outdoor conditions.

'Fislada' was selected as one flowering plant within the progeny of the stated cross in the spring of 2004 in a controlled environment in Galdar, Gran Canaria, Spain.

The first act of asexual reproduction of 'Fislada' was accomplished when vegetative cuttings were taken from the initial selection in the fall of 2004 in a controlled environment in Galdar, Gran Canaria, Spain.

Horticultural examination of plants grown from cuttings of the plant initiated in February 2005 in Hillscheid, Germany, and continuing thereafter, has demonstrated that the combination of characteristics as herein disclosed for 'Fislada' are firmly fixed and are retained through successive generations of asexual reproduction.

'Fislada' has not been observed under all possible environmental conditions. The phenotype may vary significantly with variations in environment such as temperature, light intensity and day length.

Plant Breeder's Rights for this cultivar was applied for in Canada on Mar. 30, 2007 and in Germany on Feb. 21, 2007. 'Fislada' has not been made publicly available more than one year prior to the filing of this application.

DESCRIPTION OF THE DRAWING

The accompanying photographic drawing shows typical flower and foliage characteristics of 'Fislada' with colors being as true as possible with an illustration of this type. The photographic drawing shows a flowering potted plant of the new variety.

DETAILED BOTANICAL DESCRIPTION

The measurements were taken in Hillscheid, Germany, on May 11, 2007 on plants that were growing in a greenhouse. Culture of these plants started in mid February 2007, when rooted cuttings were planted into 12 cm pots, and were pinched once in late February, and grown out at a minimum day/night temperature of (only) 14° C. until mid April, and at higher temperatures thereafter.

Color Chart used: Royal Horticultural Society Colour Chart (R.H.S.) 2001

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* plant as a new and distinct variety.

1. Brilliant, purple-pink flower color
2. Large, double-type flowers
3. Medium sized inflorescences, not very high above the foliage
4. Medium green leaves with distinct lobes and distinct zonation
5. Healthy foliage with good heat tolerance
6. Compact and tight, spreading to semi-trailing plant habit
7. Early flowering and floriferous throughout the summer

TABLE 1

DIFFERENCES BETWEEN THE NEW VARIETY 'FISLADA' AND A SIMILAR VARIETIES:

| | 'Fislada' | 'Fislina' (Parent) | 'Fisrimba' (U.S. Plant Pat. No. 12,355) |
|---|---|---|---|
| Flower color (RHS) | | | |
| Upper petals | Near N57B | 52A-B; | 58B; |
| Lower petals | Between N57B and C | 55A | N57C |
| Peduncles, length | 10.8 cm | 10.2 cm | 12.5 cm |
| Leaf shape | Ivy-shaped with distinct lobes | Nearly round, very weak lobes | Ivy-shaped, weak to medium lobes |
| Propagation, shoot tip cuttings, quality | Better stability of shoot tip chlorophyll at high temperature-better quality of cuttings | Intermediate with regard to heat tolerance of shoot tips | Tendency to develop nearly white shoot tips at high temperature |

| | 'Fislada' | 'Fislamda' (U.S. Plant Pat. No.12,225) | 'Free Cherry Rose' (U.S. Plant Pat. No. 12,448) |
|---|---|---|---|
| Flower color (RHS) | Near N57B<br>Between N57B and C | 67A<br>67B | N57B<br>N57B to N57C |
| Petal markings | Relatively strong | Strong | Weak |
| Flower size | 5.8 cm | 5.3 cm, | 4.8 cm |
| No of petals | 10-13 | over 20 | More than 20 |
| Leaf zone | Medium | Medium | Very weak |

Plant:

*Form, growth and habit.*—Well-branched, tight and compact, spreading to semi-trailing plant habit, small to medium sized.

*Plant height.*—12.7 cm.

*Plant height (inflorescence included).*—Approximately 18 cm.

*Plant diameter.*—19.3 cm.

*Plant size at the end of the summer (about 6 months old, plant spread from base of the main stem to the shoot tips).*—50–60 cm.

Stem:

*Number of branches.*—8.2.

*Color of stem.*—Light green, RHS 143B.

*Length of stem.*—12–16 cm.

*Diameter.*—0.4–0.5 cm at mid portion.

*Length of internodes.*—1–2.5 cm.

*Texture.*—Appears nearly glabrous, sparse short hair.

Foliage:

*Immature, leaf color, upper surface.*—RHS 137D. Lower surface: RHS 143B.

*Mature, leaf color, upper surface.*—RHS 137C. Lower surface: RHS 143A.

*Shape.*—Distinctly ivy-shaped, with relatively strong lobes, leaf blade is not flat, but a little folded, palmate venation.

*Base shape.*—Cordate, open gap between lowest lobes.

*Apex shape.*—Rounded, lobes with broadly acute tips.

*Margin.*—Mostly entire, single notches may occur.

*Texture.*—Glossy, glabrous.

*Color of zone.*—RHS 166A.

*Color of veins, upper surface.*—RHS 144A, indistinct.

*Color of veins, lower surface.*—RHS 145A, pale green.

*Petiole color.*—Grass-green, RHS 143A.

*Petiole length.*—Approximately 4–6 cm.

*Diameter of petiole.*—2–3 mm.

*Texture.*—Covered with weak pubescence.

Inflorescence:

*Begin of flowering (50% of plants with open flowers).*—April 25 (11 weeks old).

*Duration of flowering.*—Continuous flowering throughout the summer.

*Type and shape of inflorescence.*—An umbel, nearly semi-spherically shaped.

*Number of inflorescences per plant.*—3–4 at the stated time, approximately 15–20 in late summer.

*Number of flowers and buds per inflorescence.*—Most often 8–10.

*Umbel diameter.*—9.3 cm.

*Umbel depth.*—6.0 cm.

*Color of peduncle.*—Grass-green, RHS 143B.

*Length of peduncle.*—10.8 cm.

*Peduncle diameter.*—3 mm.

*Texture.*—Appears nearly glabrous, sparse, short hair.

*Color of pedicel.*—Mainly green, RHS 143A, partly brown, RHS 174A.

*Length of pedicel.*—2.3 cm.

*Diameter of pedical.*—1.5 mm.

*Texture.*—Very short pubescence, with a 'joint' in the middle portion.

Corolla:

*Form.*—Zygomorphic, occasionally with a gap between upper and lower petals.

*Length of flower.*—5.8 cm.

*Depth of flower.*—Approximately 2 cm.

*Number of petals.*—10–13.

*Color upper petals, upper surface.*—Slightly lighter than RHS N57B, At the base 2 purple veins (RHS 71A) with a pale purple (RHS 73C) stripe between.

*Color upper petals, lower surface.*—N58B, dull red veins, RHS 53C.

*Length of upper petals.*—3.3–3.5 cm.

*Width of upper petals.*—2.2–2.5 cm.

*Color lower petals, upper surface.*—Between RHS N57B and 57C, no markings.

*Color lower petals, lower surface.*—N58B.

*Length of lower petals.*—2.9–3.2 cm.

*Width of lower petals.*—2.0–2.2 cm.

*Petal shape.*—Obovate.

*Apex shape.*—Rounded.
*Margin.*—Entire.
*Petal texture.*—Smooth, glabrous.
*Number of petaloids.*—1–3, shorter and narrower than the petals.
*Color of petaloids.*—RHS N57B to N57C.

Bud (just before opening):
*Color.*—RHS 58B.
*Length.*—26 mm.
*Width.*—12 mm.
*Shape.*—Elliptic.

Calyx:
*Number of sepals.*—5.
*Color of sepals.*—Mainly RHS 143B, largest sepal RHS 146B.
*Length of sepals.*—14–17 mm.
*Width of sepals.*—7 mm for the largest sepal, 4 to 5 mm for the other ones.
*Sepal shape.*—Lanceolate.
*Apex shape.*—Acute, pointed.
*Margins.*—Entire.
*Texture.*—Sparse hair, relatively long, fine hairs.

Reproductive organs:
*Pistil.*—One.
*Length.*—9–11 mm.
*Style color.*—Whitish, RHS 69D.
*Style length.*—4–5 mm.
*Stigma color.*—RHS 53C, reddish.
*Number of anthers.*—Up to 10.
*Length of anthers.*—2 mm.
*Anther color.*—RHS 54A, pink.
*Length of filaments.*—9–10 mm.
*Color of filaments.*—White, RHS 155A.
*Pollen amount.*—Moderate.
*Color of pollen.*—Orange, RHS 22A.
*Fertility/seed set.*—No seed set observed.

Disease/pest resistance: Disease resistance or susceptibility has not been observed on this hybrid.

What is claimed is:

1. A new and distinct variety of *Pelargonium* plant named 'Fislada,' substantially as illustrated and described herein.

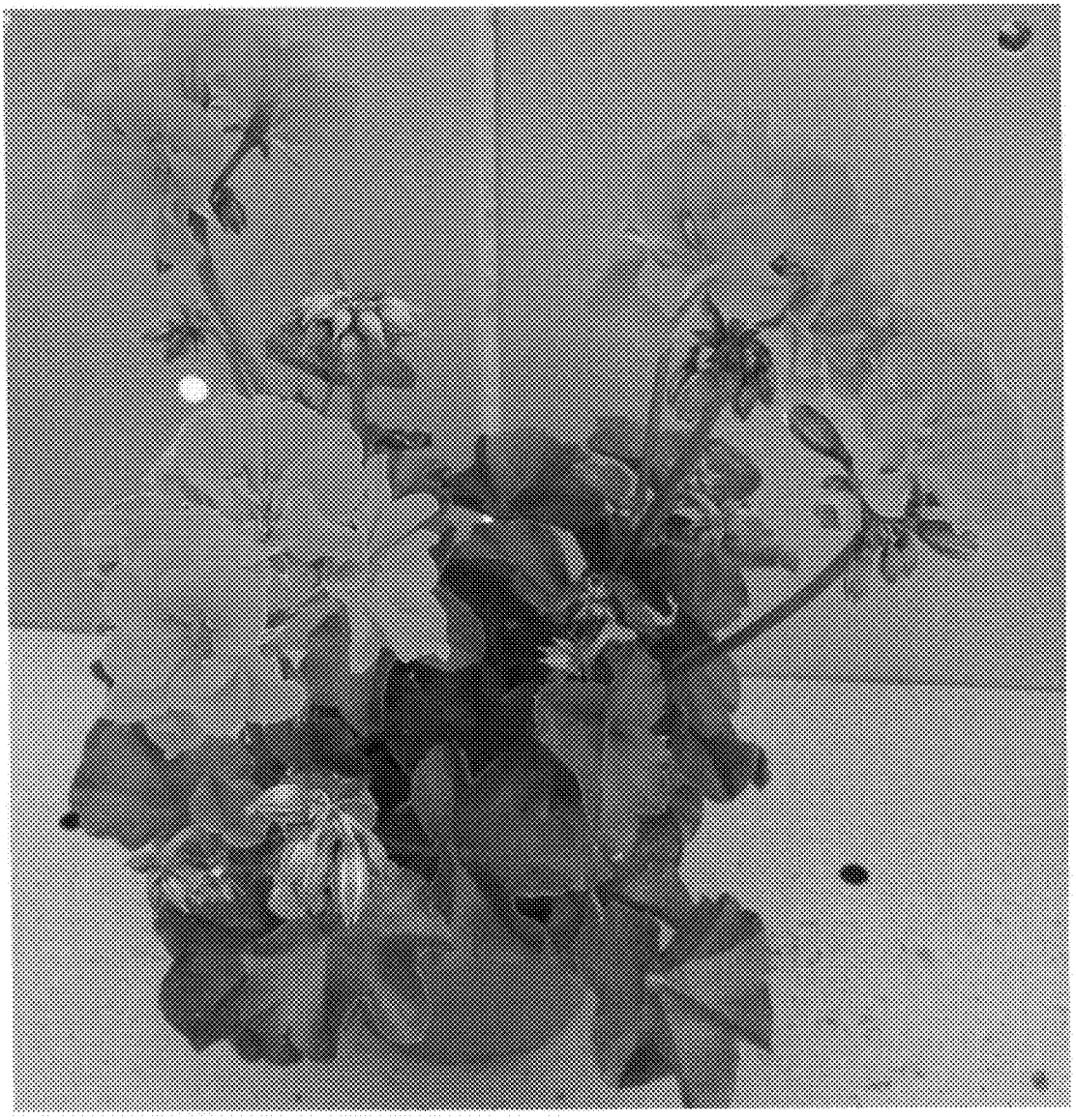

* * * * *